US011607181B2

(12) United States Patent
Sha et al.

(10) Patent No.: US 11,607,181 B2
(45) Date of Patent: Mar. 21, 2023

(54) SYSTEMS AND METHODS FOR CARDIAC TRIGGERING OF AN IMAGING SYSTEM

(71) Applicant: General Electric Company, Schenectady, NY (US)

(72) Inventors: Liewei Sha, Hartland, WI (US); Dawei Gui, Sussex, WI (US); Yawei Liu, Oconomowoc, WI (US); Yan Ma, Brookfield, WI (US); Haonan Wang, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 709 days.

(21) Appl. No.: 16/041,462

(22) Filed: Jul. 20, 2018

(65) Prior Publication Data
US 2020/0022660 A1 Jan. 23, 2020

(51) Int. Cl.
A61B 5/00 (2006.01)
A61B 5/055 (2006.01)
A61B 5/316 (2021.01)
A61B 5/352 (2021.01)

(52) U.S. Cl.
CPC .......... A61B 5/7285 (2013.01); A61B 5/0044 (2013.01); A61B 5/055 (2013.01); A61B 5/316 (2021.01); A61B 5/352 (2021.01); A61B 5/7221 (2013.01); A61B 5/7264 (2013.01)

(58) Field of Classification Search
CPC ................ A61B 5/7285; A61B 5/0456; A61B 5/04012; A61B 5/7221; A61B 5/055; A61B 5/0044; A61B 5/7264; A61B 5/04525; A61B 5/7292; A61B 5/0402; A61B 5/7267; A61B 2576/023; G16H 50/20
See application file for complete search history.

(56) References Cited

U.S. PATENT DOCUMENTS

| 7,738,943 B2 | 6/2010 | Sha et al. | |
| 2004/0073124 A1* | 4/2004 | Axel | A61B 5/35 600/509 |
| 2005/0222508 A1* | 10/2005 | Moreno | A61B 5/7264 600/509 |
| 2010/0191134 A1* | 7/2010 | Frank | A61B 5/7285 600/521 |
| 2016/0106332 A1* | 4/2016 | Takeshima | A61B 5/366 600/509 |

(Continued)

FOREIGN PATENT DOCUMENTS

CN 101953682 A * 1/2011
WO WO-2016142793 A1 * 9/2016 ......... A61B 5/02405

Primary Examiner — Yi-Shan Yang
Assistant Examiner — Nicholas A Robinson
(74) Attorney, Agent, or Firm — Fletcher Yoder P.C.

(57) ABSTRACT

Methods and systems are provided for cardiac triggering of an imaging system. a method for an imaging system comprises acquiring, during a scan of a subject, an electrical signal indicating a periodic physiological motion of an organ of the subject, inputting a sample of the electrical signal into a trained neural network to detect whether a peak is present in the sample, triggering acquisition of image data responsive to detecting the peak in the sample, and not triggering the acquisition of image data responsive to not detecting the peak in the sample. In this way, the timing of data acquisition may be optimally and robustly synchronized with a cardiac cycle.

15 Claims, 8 Drawing Sheets

(56) References Cited

U.S. PATENT DOCUMENTS

| | | | |
|---|---|---|---|
| 2016/0128643 A1* | 5/2016 | Yoshida | A61B 5/352 600/413 |
| 2016/0361041 A1* | 12/2016 | Barsimantov | G16H 50/30 |
| 2017/0086752 A1* | 3/2017 | Baxi | A61B 5/316 |
| 2018/0000424 A1* | 1/2018 | Demirtas | A61B 5/6802 |
| 2018/0196932 A1* | 7/2018 | Zhang | A61B 5/7264 |

* cited by examiner

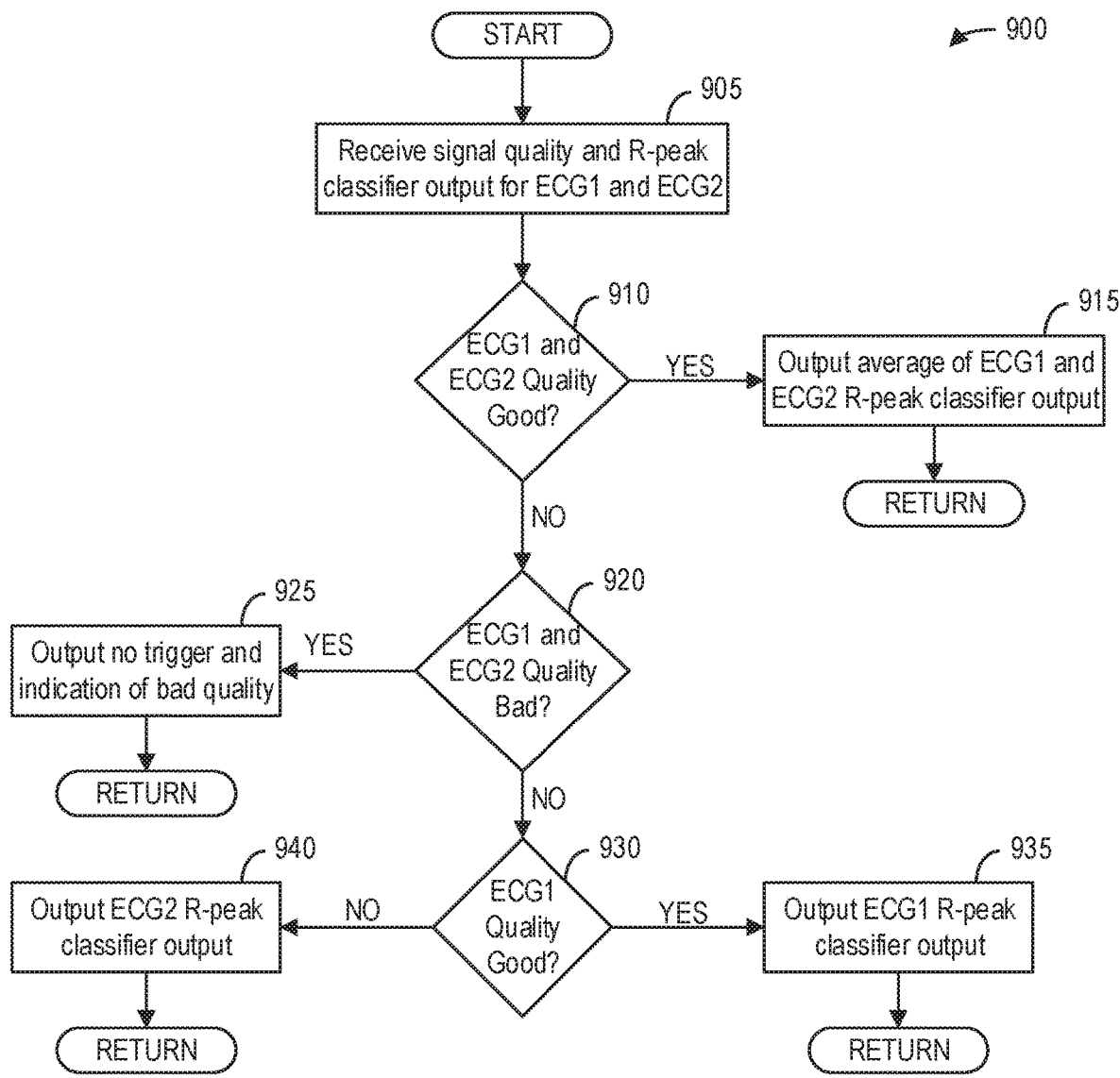

SYSTEMS AND METHODS FOR CARDIAC TRIGGERING OF AN IMAGING SYSTEM

FIELD

Embodiments of the subject matter disclosed herein relate to medical imaging, such as magnetic resonance imaging (MM), and more particularly, to triggering data acquisition according to a cardiac cycle.

BACKGROUND

Medical imaging systems are often used to obtain internal physiological information of a subject, such as a patient. For example, a medical imaging system may be used to obtain images of the bone structure, the brain, the heart, the lungs, and various other features of a subject. Medical imaging systems magnetic resonance imaging (MM) systems, computed tomography (CT) systems, x-ray systems, ultrasound systems, and various other imaging modalities.

It is often desirable to obtain an image at a particular point in a variable cycle, such as a peak of the variable cycle, to analyze behavior at that peak. Gating is an option for characterizing different attributes of an organ for imaging. The most common techniques of gating include cardiac, respiratory, and peripheral pulse gating, and these types of gating have uses in numerous medical applications across diagnostic modalities such as CT, MR, x-ray, ultrasound, and position emission tomography (PET). Cardiac gating, as a specific example, is an essential component of cardiac imaging while using imaging modalities such as CT and MR to minimize motion-related artifacts.

BRIEF DESCRIPTION

In one embodiment, a method for an imaging system comprises acquiring, during a scan of a subject, an electrical signal indicating a periodic physiological motion of an organ of the subject, inputting a sample of the electrical signal into a trained neural network to detect whether a peak is present in the sample, triggering acquisition of image data responsive to detecting the peak in the sample, and not triggering the acquisition of image data responsive to not detecting the peak in the sample. In this way, the timing of data acquisition may be optimally and robustly synchronized with the cardiac cycle.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 9 shows a high-level flowchart illustrating an example method for determining a trigger according to an embodiment.

DETAILED DESCRIPTION

Figure 6:
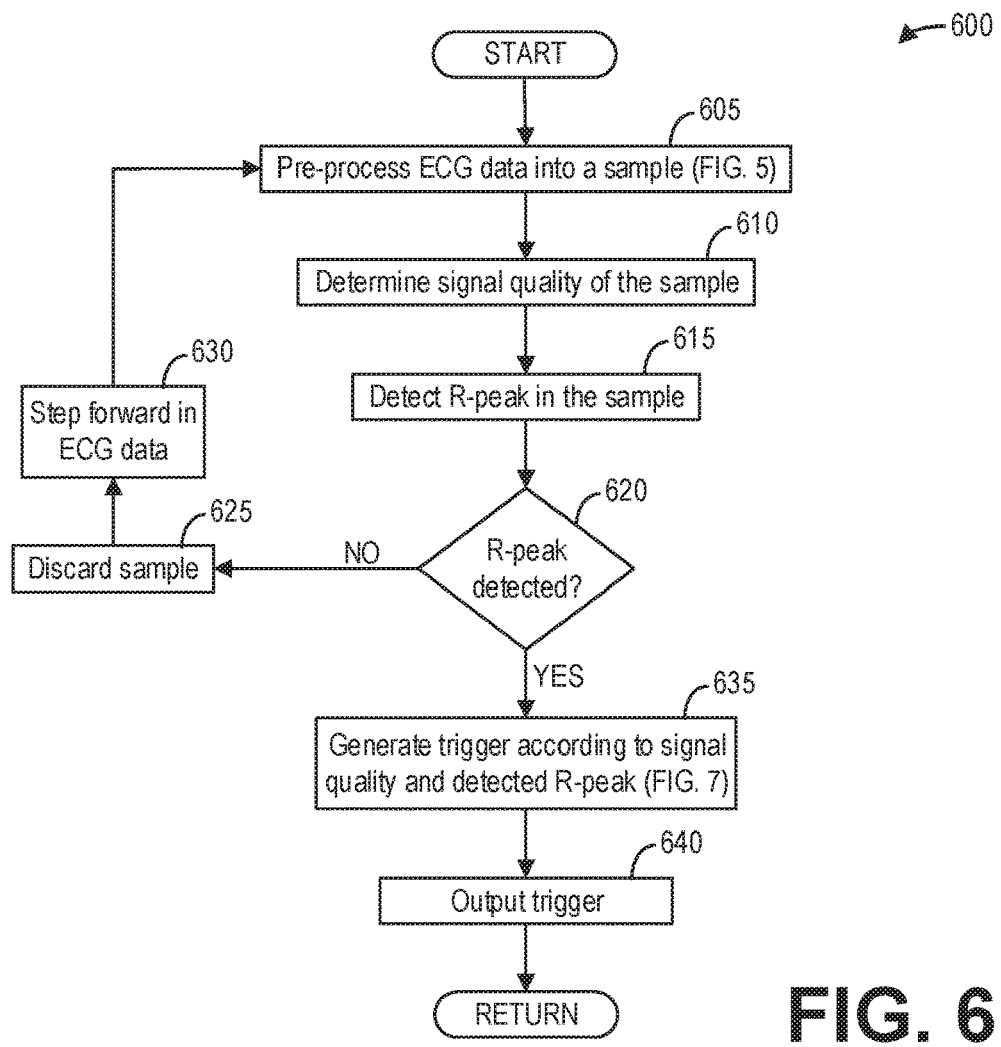
FIG. 6 shows a high-level flow chart illustrating an example method for generating a trigger from ECG data according to an embodiment.
Figure 7:
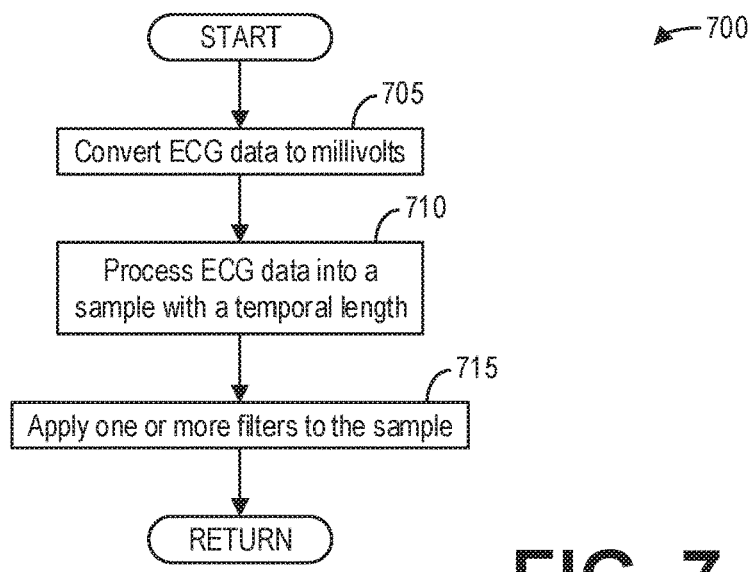
FIG. 7 shows a high-level flow chart illustrating an example method for pre-processing ECG data for triggering MR data acquisition according to an embodiment.
Figure 8:
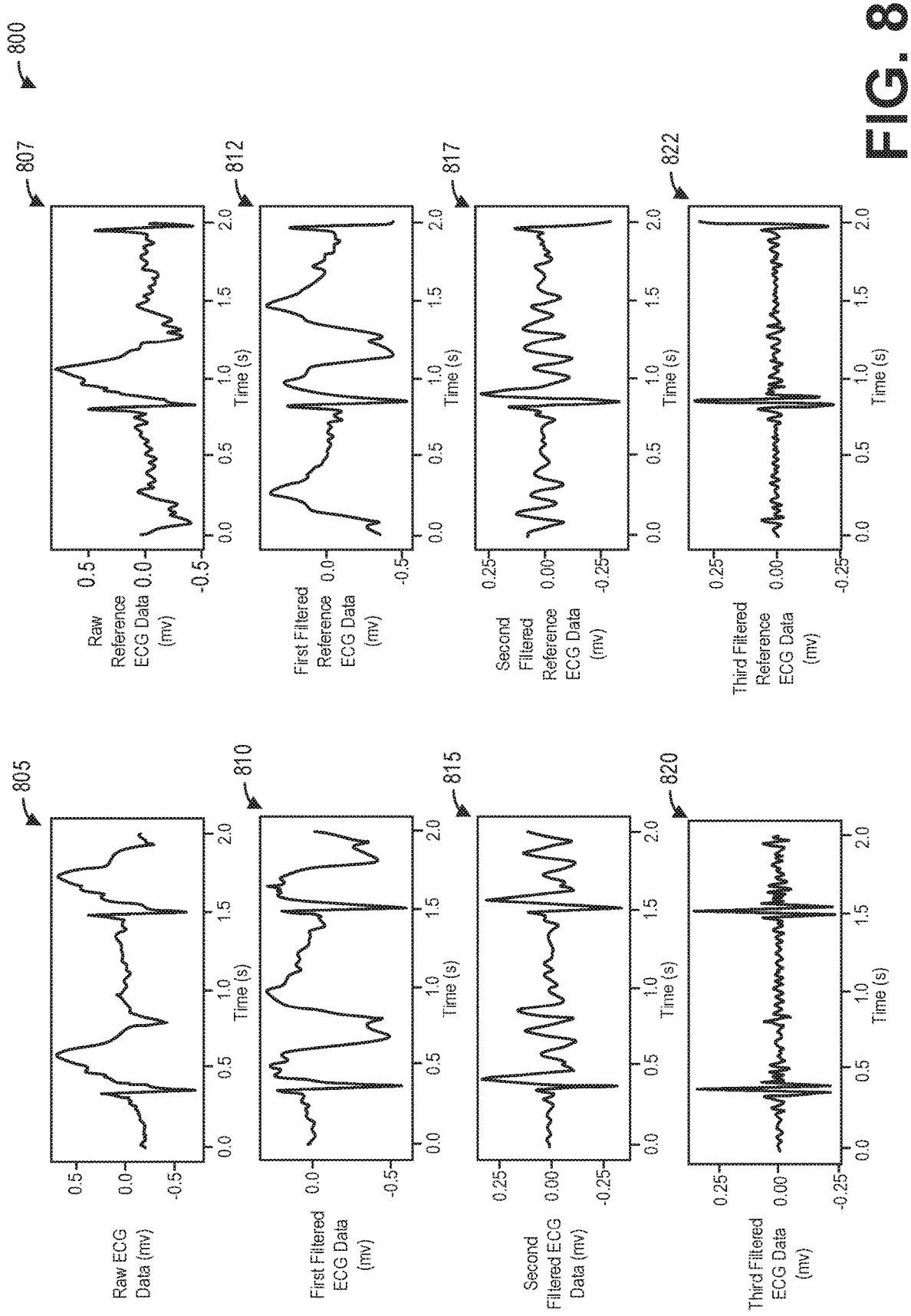
FIG. 8 shows a set of graphs illustrating raw ECG data and filtered ECG data by different filters according to an embodiment.

The following description relates to various embodiments of triggering data acquisition for imaging systems. In particular, systems and methods are provided for triggering data acquisition according to an electrocardiographic (ECG) signal with an imaging system, such as the MRI system depicted in FIG. 1. Multiple channels of an ECG signal may be simultaneously input to different deep learning classifiers for determining signal quality of the ECG signal as well as detecting R-peaks in the ECG signal, as depicted in FIG. 2. The deep learning classifiers may comprise one or more neural networks, such as the neural network depicted in FIG. 3, which may include a large plurality of nodes or neurons, such as the neuron depicted in FIG. 4. The deep learning classifiers in particular may comprise one or more convolutional neural networks, which may include a plurality of unit layers. A method for performing a diagnostic scan, such as the method depicted in FIG. 5, may include acquiring ECG data prior to a scan to use as a reference for the R-peak detection. The ECG signal is sampled over a duration, and may be iteratively re-sampled until an R-peak is detected, as illustrated in FIG. 6. The samples of the ECG signal may be pre-processed prior to classification, as depicted in FIG. 7, to simplify the detection of the R-peak. Pre-processing the sample may include applying passband filters, as depicted in FIG. 8. The data acquisition trigger may be determined according to different combinations of the output of the peak detection classifiers, depending on the signal quality of the samples, as depicted in FIG. 9.

Figure 1:
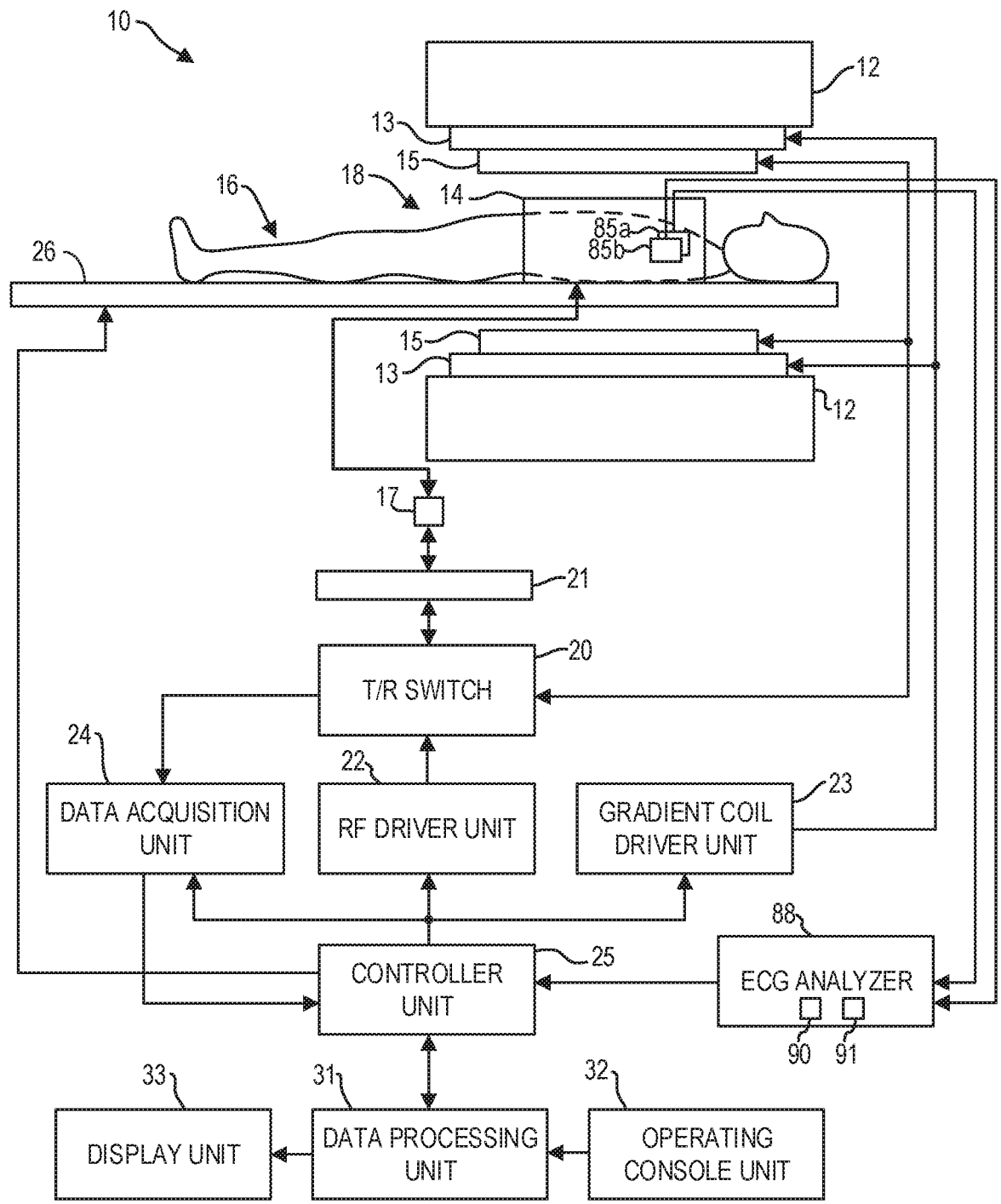
FIG. 1 is a block diagram of an MRI system according to an embodiment.
Figure 2:
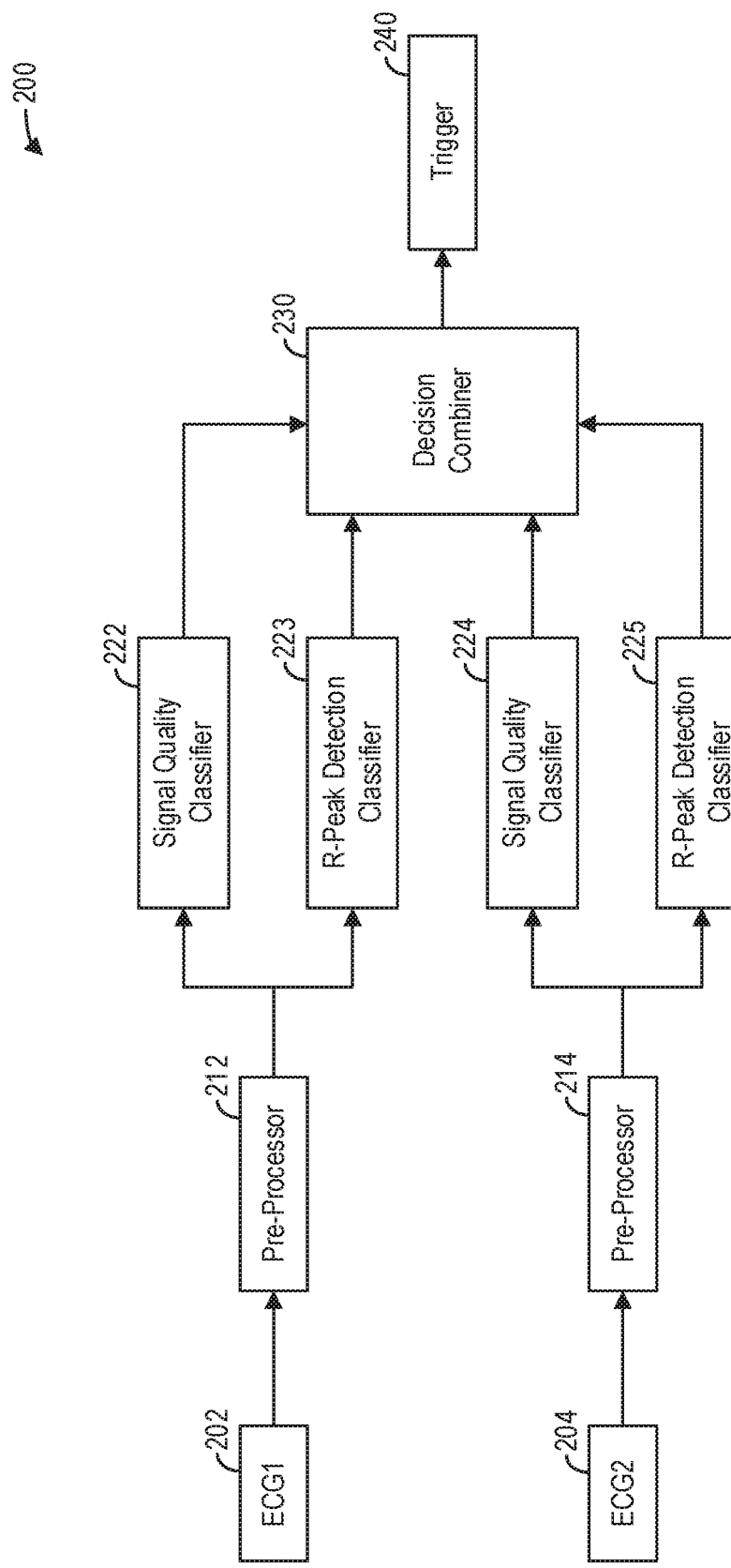
FIG. 2 shows a block diagram illustrating an example system for triggering MR data acquisition based on periodic physiological motion of a subject according to an embodiment.

FIG. 1 illustrates a magnetic resonance imaging (MM) apparatus 10 that includes a magnetostatic field magnet unit 12, a gradient coil unit 13, a local RF coil unit 14, an RF body coil unit 15, a transmit/receive (T/R) switch 20, an RF port interface 21, an RF driver unit 22, a gradient coil driver unit 23, a data acquisition unit 24, a controller unit 25, a patient bed 26, a data processing unit 31, an operating console unit 32, and a display unit 33. The MRI apparatus 10 transmits electromagnetic pulse signals to a subject 16 placed in an imaging space 18 with a magnetostatic field formed to perform a scan for obtaining magnetic resonance (MR) signals from the subject 16 to reconstruct an image of the slice of the subject 16 based on the MR signals thus obtained by the scan.

The magnetostatic field magnet unit 12 includes, for example, typically an annular superconducting magnet, which is mounted within a toroidal vacuum vessel. The magnet defines a cylindrical space surrounding the subject 16, and generates a constant primary magnetostatic field $B_0$.

The MM apparatus 10 also includes a gradient coil unit 13 that forms a gradient magnetic field in the imaging space 18 so as to provide the magnetic resonance signals received by the RF coil unit 14 with three-dimensional positional information. The gradient coil unit 13 includes three gradient coil systems, each of which generates a gradient magnetic field which inclines into one of three spatial axes perpendicular to each other, and generates a gradient field in each of frequency encoding direction, phase encoding direction, and slice selection direction in accordance with the imaging condition. More specifically, the gradient coil unit 13 applies a gradient field in the slice selection direction (or scan direction) of the subject 16, to select the slice; and the RF body coil unit 15 or the local RF coil unit 14 may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The local RF coil unit 14 is disposed, for example, to enclose the region to be imaged of the subject 16. In the static magnetic field space or imaging space 18 where a static magnetic field $B_0$ is formed by the magnetostatic field magnet unit 12, the local RF coil unit 14 transmits, based on a control signal from the controller unit 25, an RF pulse that is an electromagnetic wave to the subject 16 and thereby generates a high-frequency magnetic field $B_1$. This excites a spin of protons in the slice to be imaged of the subject 16. The local RF coil unit 14 receives, as a magnetic resonance signal, the electromagnetic wave generated when the proton spin returns into alignment with the initial magnetization vector. In one embodiment, the local RF coil unit 14 may transmit and receive an RF pulse using the same local RF coil. In another embodiment, the local RF coil may be used for only receiving the MR signals, but not transmitting the RF pulse.

The RF body coil unit 15 is disposed, for example, to enclose the imaging space 18, and produces RF magnetic field pulses $B_1$ orthogonal to the main magnetic field $B_0$ produced by the magnetostatic field magnet unit 12 within the imaging space 18 to excite the nuclei. In contrast to the local RF coil unit 14, which may be easily disconnected from the MRI apparatus 10 and replaced with another local RF coil unit, the RF body coil unit 15 is fixedly attached and connected to the MRI apparatus 10. Furthermore, whereas local coils such as those comprising the RF coil unit 14 can transmit to or receive signals from only a localized region of the subject 16, the RF body coil unit 15 generally has a larger coverage area and can be used to transmit or receive signals to the whole body of the subject 16. Using receive-only local coils and transmit body coils provides a uniform RF excitation and good image uniformity at the expense of high RF power deposited in the subject 16. For a transmit-receive local coil, the local coil provides the RF excitation to the region of interest and receives the MR signal, thereby decreasing the RF power deposited in the subject 16. It should be appreciated that the particular use of the local RF coil unit 14 and/or the RF body coil unit 15 depends on the imaging application.

The T/R switch 20 can selectively electrically connect the RF body coil unit 15 to the data acquisition unit 24 when operating in a receive mode, and to the RF driver unit 22 when operating in transmit mode. Similarly, the T/R switch 20 can selectively electrically connect the local RF coil unit 14 to the data acquisition unit 24 when the local RF coil unit 14 operates in receive mode, and to the RF driver unit 22 when operating in transmit mode. When the local RF coil unit 14 and the RF body coil unit 15 are both used in a single scan, for example if the local RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the local RF coil unit 14 to the data acquisition unit 24. The RF body coil unit 15 may be configured to operate in a transmit-only mode, a receive-only mode, or a transmit-receive mode. The local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coil unit 14 and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 14.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a preamplifier (not shown), a phase detector (not shown), and an analog/digital converter (not shown) used to acquire the MR signals received by the local RF coil unit 14. In the data acquisition unit 24, the phase detector phase detects, using the output from the RF oscillator of the RF driver unit 22 as a reference signal, the MR signals received from the RF coil unit 14 and amplified by the preamplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25. One or more of the RF coil arrays may be coupled to the table 26 and moved together with the table.

The controller unit 25 includes a computer and a recording medium on which a program to be executed by the computer is recorded, in some embodiments. The program when executed by the computer causes various parts of the apparatus to carry out operations corresponding to predetermined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a slice image of the subject 16 generated by the data processing unit 31.

Different local RF coil units may be utilized for different scanning objectives. To that end, the local RF coil unit 14 may be disconnected from the MRI apparatus 10, so that a different local coil unit may be connected to the MM apparatus 10. The RF coil unit 14 may be coupled to the T/R switch 20, and thus to the RF driver unit 22 and the data acquisition unit 24, via a connector 17 and an RF port interface 21. The connector 17 may be plugged into the RF port interface 21 to electronically couple the local RF coil unit 14 to the T/R switch 20.

The MRI apparatus 10 further includes a set of electrocardiographic (ECG) sensors 85a and 85b coupled to an ECG signal analyzer 88. The ECG sensors 85a and 85b are positioned on the subject 16 adjacent to a heart (not shown) of the subject 16 and are electrically coupled to the ECG signal analyzer 88, such that the ECG sensors 85a and 85b sense electrical activity of the heart of the subject 16 over time and transmits corresponding ECG signals to the ECG signal analyzer 88. The ECG sensor 85a comprises a first lead set and the ECG sensor 85b comprises a second lead set. In some examples, each lead set may comprise two leads, such that the first lead set or ECG sensor 85a includes two leads while the second lead set or ECG sensor 85b includes two leads. In other examples, each lead set may include a single lead, while an additional, third lead (not shown) is shared by both ECG sensors 85a and 85b as a ground lead.

The ECG signal analyzer 88 analyzes the ECG signals received from the ECG sensors 85a and 85b to generate a trigger for controlling a scan of the subject 16, as described further herein. To that end, the ECG signal analyzer 88 comprises a processor 90 and a memory 91 such as a non-transitory memory for storing executable instructions. Although a single processor 90 and a single memory 91 are depicted, it should be appreciated that the ECG signal analyzer 88 may include any suitable number of processors 90 and memories 91.

As mentioned above and described further herein, the ECG signals may be used to generate the gating pulse or trigger for MR data acquisition. For example, the R-wave of the ECG signal may be used for this purpose. A cardiac cycle is typically defined as beginning with an R-wave and continuing until the occurrence of another R-wave. Triggering MR data acquisition based on detection of an R-wave allows image acquisition during the scan to be gated such that image data is acquired only during periods of the cardiac cycle for which the heart is nearly stationary.

FIG. 2 shows a block diagram illustrating an example system 200 for triggered MR data acquisition based on periodic physiological motion of a subject. The system 200 may comprise, for example, an ECG signal analyzer such as ECG signal analyzer 88, and so the system 200 is described with reference to the systems and components of FIG. 1, though it should be understood that the system 200 may be implemented with other systems and components without departing from the scope of the present disclosure. For example, the components of the system 200 may be implemented as software modules or executable instructions in the non-transitory memory 91 of the ECG signal analyzer 88, and may be executed by the processor 90 of the ECG signal analyzer 88 to perform the functions described herein.

The system 200 includes a first ECG signal (ECG1) 202 and a second ECG signal (ECG2) 204, which may be respectively generated by ECG sensors such as ECG sensors 85a and 85b. For example, the first ECG signal 202 may be generated by the ECG sensor 85a while the second ECG signal 204 may be generated by the ECG sensor 85b. Although only two channels or ECG signals are depicted, it should be appreciated that more than two ECG signals may be used in some examples.

The system 200 further comprises a first pre-processor 212 and a second pre-processor 214. The first pre-processor 212 and the second pre-processor 214 pre-process the first ECG signal 202 and the second ECG signal 204, respectively, as depicted. For example, the first ECG signal 202 and the second ECG signal 204 may comprise continuous electronic signals received from the ECG sensors 85a and 85b, and the first pre-processor 212 and the second pre-processor 214 discretely sample the ECG signals 202 and 204, respectively, to form samples of a given temporal length. For example, a sample generated by the first pre-processor 212 may comprise a plurality of discrete measurements of the first ECG signal 202 over a given temporal length such as two or three seconds. The given temporal length may be selected to at least approximately correspond to a typical duration of a cardiac cycle, such that an R-peak may be expected to be observed in the sample. In some examples, the given temporal length may be less than the typical duration of a cardiac cycle, such that the observation of two R-peaks within a single sample is highly unlikely.

A sample may include, as an illustrative and non-limiting example, one thousand or two thousand discrete measurements or samples of the ECG signal. For example, the pre-processor 212 may sample the first ECG signal 202 every other millisecond to collect one thousand measurements for the sample in a two second duration, or as another example, the pre-processor 212 may sample the first ECG signal 202 every millisecond to collect two thousand measurements for the sample in the two second duration. Furthermore, the pre-processors 212 and 214 may apply one or more filters such as passband filters to the sample to generate one or more filtered samples.

In addition, the pre-processors 212 and 214 may pre-process a reference sample of the ECG signal acquired from the subject prior to a scan. The reference sample may include the same number of measurements (e.g., one or two thousand measurements over the given temporal length) and may be similarly filtered. The reference sample may be preprocessed such that an R-peak is observable near the end of the time window of the sample. For example, the reference sample may be configured such that the R-peak occurs twenty milliseconds before the end of the time window. An example reference sample and real-time sample are described further herein with regard to FIG. 8.

The system 200 further includes a first signal quality classifier 222 and a second signal quality classifier 224 for evaluating the signal quality of the first ECG signal 202 and the second ECG signal 204, respectively. The first signal quality classifier 222 and the second signal quality classifier 224 may comprise, for example, convolutional neural networks configured to receive the real-time sample (i.e., the pre-processed sample of the ECG signal measured in real-time during the scan) and output an indication that the signal quality of the real-time sample is good or bad. The output of the convolution neural networks may comprise two nodes, wherein one node corresponds to a good signal quality and the other node corresponds to a bad signal quality.

Figure 3:
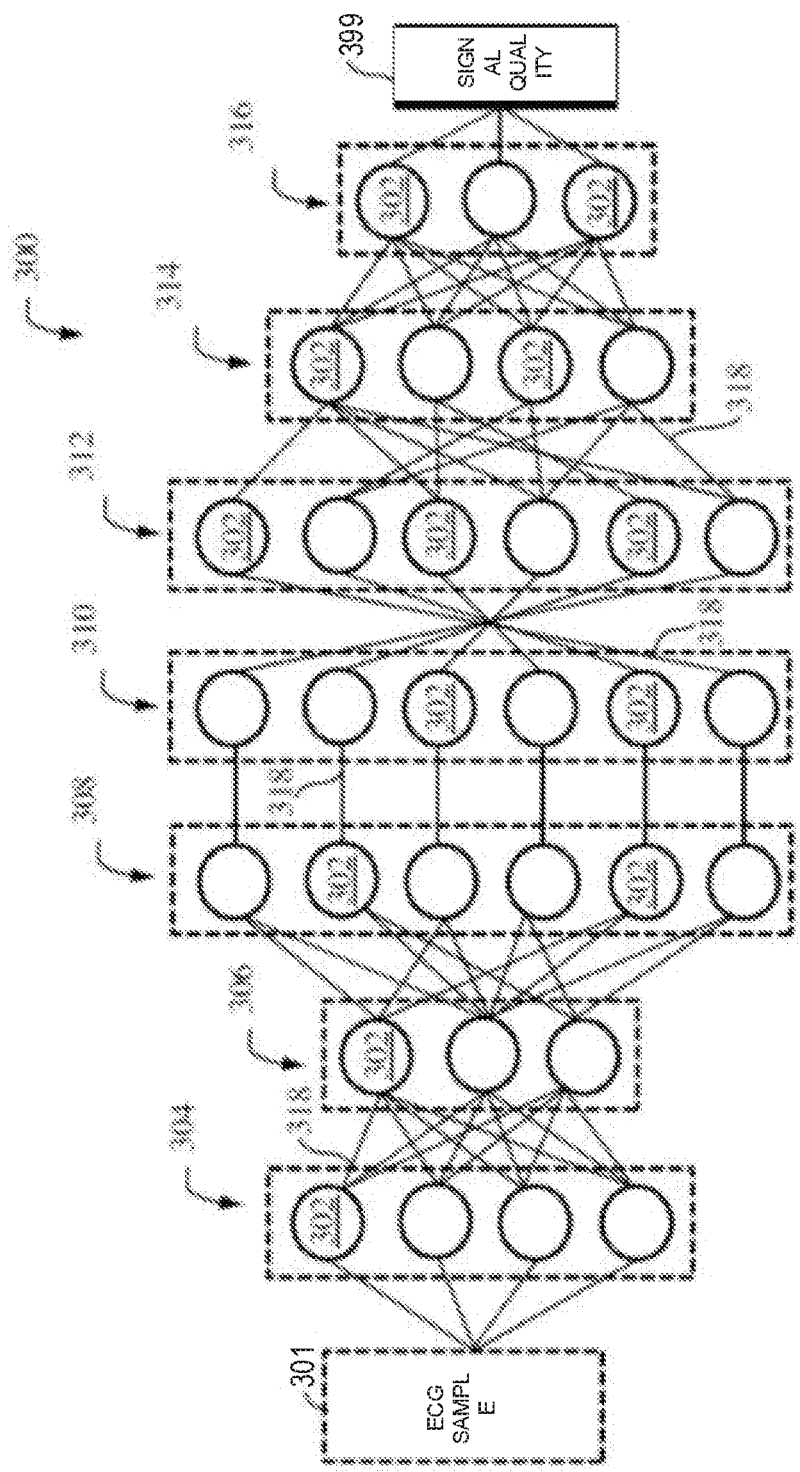
FIG. 3 shows a block diagram illustrating an example neural network according to an embodiment.

As an illustrative example, FIG. 3 depicts a neural network 300 having one or more nodes/neurons 302 which, in some embodiments, may be disposed into one or more layers 304, 306, 308, 310, 312, 314, and 316. The neural network 300 may be a deep neural network. As used herein with respect to neurons, the term "layer" refers to a collection of simulated neurons that have inputs and/or outputs connected in similar fashion to other collections of simulated neurons. Accordingly, as shown in FIG. 3, the neurons 302 may be connected to each other via one or more connections 318 such that data may propagate from an input layer 304, through one or more intermediate layers 306, 308, 310, 312, 314 to an output layer 316.

Figure 4:
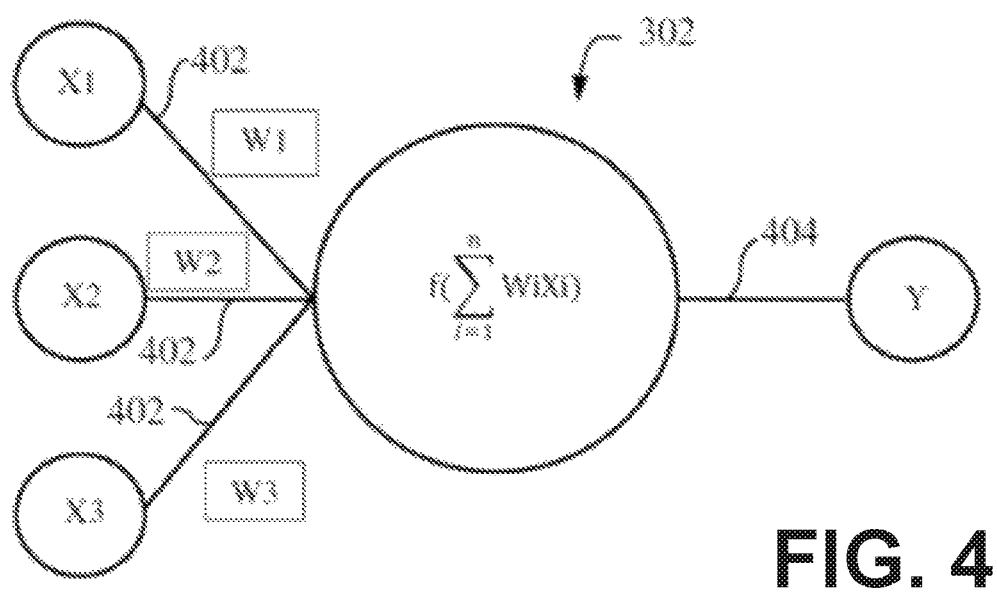
FIG. 4 shows a block diagram illustrating an example node of a neural network according to an embodiment.

FIG. 4 shows input and output connections for a neuron in accordance with an exemplary embodiment. As shown in FIG. 4, the connections 318 of an individual neuron 302 may include one or more input connections 402 and one or more output connections 404. Each input connection 402 of a neuron 302 may be an output connection of a preceding neuron, and the output connections 404 of the neuron 302 may be an input connection of one or more subsequent neurons. While FIG. 4 depicts a neuron 302 as having a single output connection 402, it should be understood that neurons may have multiple output connections that transmit/pass the same value. In embodiment, the neurons 302 may be data constructs, e.g., structures, instantiated class objects, matrices, etc., and the input connections 318 may be received by the neuron 302 as weighted numerical values, e.g., floating point or integer values. For example, as further shown in FIG. 4, input connections X1, X2, and X3 may be weighted via weights W1, W2, and W3, respectively, summed, and sent/transmitted/passed as output connection Y. As will be appreciated, the processing of an individual neuron 302 may be represented, generally, by the equation:

$$Y = f\left(\sum_{i=1}^{n} W_i X_i\right)$$

where n is the total number of input connections 402 to the neuron 302. In embodiment, the value of Y may be based at least in part on whether the summation of WiXi exceeds a threshold. For example, Y may have a value of zero (0) if the summation of the weighted inputs fails to exceed a desired threshold.

As will be further understood, the input connections 402 of neurons 302 in the input layer 304 may be mapped to the input 301, while the output connections 402 of the neurons 302 in the output layer 316 may be mapped to the output 399. As used herein, "mapping" an input connection 402 to the input 301 refers to the manner by which the input 301 affects/dictates the value of the input connections 402. Similarly, as also used herein, "mapping" an output connection 402 to the output 399 refers to the manner by which the value of the output connections 402 affects the output 399.

Accordingly, in embodiments, the acquired/obtained input 301 is passed/fed to the input layer 304 of the neural network 300 and propagated through the layers 304, 306, 308, 310, 312, 314, and 316 such that mapped output connections 404 of the output layer 316 generates/corresponds to the output 399.

As a more detailed illustrative example of how the neural network 300 may be constructed as a convolutional neural network for the signal quality classifiers 222 and 224, an example architecture for a convolutional neural network may be used. In some examples, the signal quality classifiers 222 and 224 may comprise convolution neural networks such as the convolutional neural network described herein. The convolutional neural network may include a first one-dimensional convolutional layer, a second one-dimensional convolutional layer, a first unit layer, a second unit layer, a third unit layer, a fourth unit layer, a fifth unit layer, a flatten layer, a dense layer, a dropout layer, and a dense output layer. Example configurations of neurons for each layer of the convolutional neural network are described further herein for embodiments wherein the convolutional neural network is configured as a signal quality classifier or an R-peak detection classifier. Furthermore, one or more layers of the convolutional neural network may be multi-dimensional (e.g., two- or three-dimensional), as discussed further herein.

The input to the convolutional neural network is mapped to each neuron of the first one-dimensional convolutional layer, which applies a convolutional operation to the input and passes the convolved result to the second one-dimensional convolutional layer. The second one-dimensional convolutional layer applies a convolutional operation to the convolved results from the first one-dimensional convolutional layer and passes the convolved result to the first unit layer. Similarly, the output of the first unit layer is passed to the second unit layer, the output of the second unit layer is passed to the third unit layer, the output of the third unit layer is passed to the fourth unit layer, the output of the fourth unit layer is passed to the fifth unit layer, the output of the fifth unit layer is passed to the flatten layer for flattening, the flattened output of the flatten layer is passed to the fully-connected or dense layer, the transformed output of the dense layer is passed to the dropout layer, the output of the dropout layer is passed to the dense output layer, and the output of the dense output layer comprises the output of the convolutional neural network.

Furthermore, the unit layers of the convolutional neural network include a plurality of steps or layers. As an illustrative example, an example architecture for a unit layer provides an input to a batch normalization layer to perform batch normalization of the input. The unit layer includes a one-dimensional convolution layer that applies a one-dimensional convolution to the output of the batch normalization layer. The unit layer further includes a one-dimensional max pooling layer that applies a max pooling to the output of the one-dimensional convolution layer. The unit layer further includes a dropout layer that drops or ignores randomly selected units or neurons during particular forward and/or backward passes to prevent overfitting. The output of the dropout layer is thus the output of the unit layer. Each of the unit layers may be constructed according to the architecture of the unit layer.

The sample may include a plurality of measurements of the ECG signal, and furthermore the sample may include the plurality of measurements with various bandpass filters applied to the raw plurality of measurements of the ECG signal. For example, the sample may include a raw sample, a first filtered sample, a second filtered sample, and a third filtered sample.

When the network, such as the example convolutional neural network, is configured as a signal quality classifier such as signal quality classifiers 222 and 224, the convolutional neural network receives the input comprising a sample and generates the output of signal quality of the sample. The table below depicts an example configuration of neurons or nodes in each of layer as well as the dimensionality of each layer of the convolutional neural network when configured as a signal quality classifier, when the input sample includes four sets (one raw, three filtered) of 2,000 measurements of the ECG signal, and the dense output layer includes two nodes indicating good or bad signal quality as discussed hereinabove.

| Signal Quality Classifier Architecture | | |
| --- | --- | --- |
| Layers | First Input Dimension | Second Input Dimension |
| First 1D Convolutional | 2000 | 4 |
| Second 1D Convolutional | 2000 | 4 |
| First Unit | 2000 | 8 |
| Second Unit | 984 | 16 |
| Third Unit | 460 | 16 |
| Fourth Unit | 166 | 16 |
| Fifth Unit | 51 | 16 |
| Flatten | 25 | 16 |
| Dense | 400 | |
| Dropout | 32 | |
| Dense | 2 | |

The convolutional neural networks may be trained with a training dataset containing a plurality of samples, wherein each sample of the plurality of samples is labeled as having good signal quality or bad signal quality. The plurality of samples for the training dataset may be manually or automatically labeled, wherein one or more features of the sample may be used to manually or automatically label the samples as having good or bad signal quality. The signal quality of a sample may be classified as bad signal quality if the sample exhibits low signal amplitude, signal truncation, motion noise, high frequency noise, and so on. In general, a sample may be classified as having bad signal quality when no R-peaks are observable via vision inspection in a time window of sufficient length such that an R-peak should be visually observable in the sample.

Referring again to FIG. 2, the system 200 further includes a first R-peak detection classifier 223 and a second R-peak detection classifier 225 for detecting the presence of an R-peak in a sample of the first ECG signal 202 and the second ECG signal 204, respectively. The first R-peak detection classifier 223 and the second R-peak detection classifier 225 may comprise convolutional neural networks configured to receive the real-time sample and the reference sample and output whether an R-peak is detected within the real-time sample. The output of the convolutional neural networks may comprise two nodes, wherein one node corresponds to the presence of an R-peak in the sample and the other node corresponds to the absence of an R-peak in the sample. In some examples, the output of the convolutional neural network may include an additional third node that corresponds to the absence of an R-peak but the presence of a noise spike. The convolutional neural networks forming the first and second R-peak detection classifiers 223 and 225 may be trained using one or more training datasets comprising a plurality of samples manually or automatically labeled as including an R-peak, not including an R-peak, or not including an R-peak but including one or more noise spikes.

The convolutional neural networks forming the first and second R-peak detection classifiers 223 and 225 may be constructed according to the architecture of the convolutional neural network and described hereinabove, with a plurality of unit layers. The table below depicts an example configuration of neurons or nodes in each of layer as well as the dimensionality of each layer of the convolutional neural network configured as an R-peak detection classifier, when the input sample includes a four sets (one raw, three filtered) of 2,000 measurements of the real-time ECG signal and the reference ECG sample, and the dense output layer includes three nodes indicating an R-peak, no R-peak, or a non-R-peak noise spike as discussed hereinabove.

| Layers | First Input Dimension | Second Input Dimension | Third Input Dimension |
| --- | --- | --- | --- |
| First 1D Convolutional | 2000 | 4 | 2 |
| Second 1D Convolutional | 2000 | 4 | 2 |
| First Unit | 2000 | 4 | 16 |
| Second Unit | 984 | 1 | 32 |
| Third Unit | 476 | 1 | 64 |
| Fourth Unit | 111 | 1 | 128 |
| Fifth Unit | 20 | 1 | 64 |
| Flatten | 5 | 1 | 32 |
| Dense | 160 | | |
| Dropout | 32 | | |
| Dense | 3 | | |

It should be appreciated that the example convolutional neural network architectures described hereinabove for both the signal quality classifiers and the R-peak detection classifiers are illustrative and non-limiting. It should further be appreciated that other types of neural networks, such as recurrent neural networks, or other types of deep learning classification algorithms other than convolutional neural networks may be used to perform signal quality classification and R-peak detection classification.

The system 200 further includes a decision combiner 230 for combining the output of the first signal quality classifier 222, the first R-peak detection classifier 223, the second signal quality classifier 224, and the second R-peak detection classifier 225. An example method for determining a trigger according to the outputs of the signal quality classifiers 222 and 224 as well as the R-peak detection classifiers 223 and 224 is described further herein with regard to FIG. 7. The decision combiner 230 outputs a trigger 240 which may be used to control the scan, as described herein.

Figure 5:
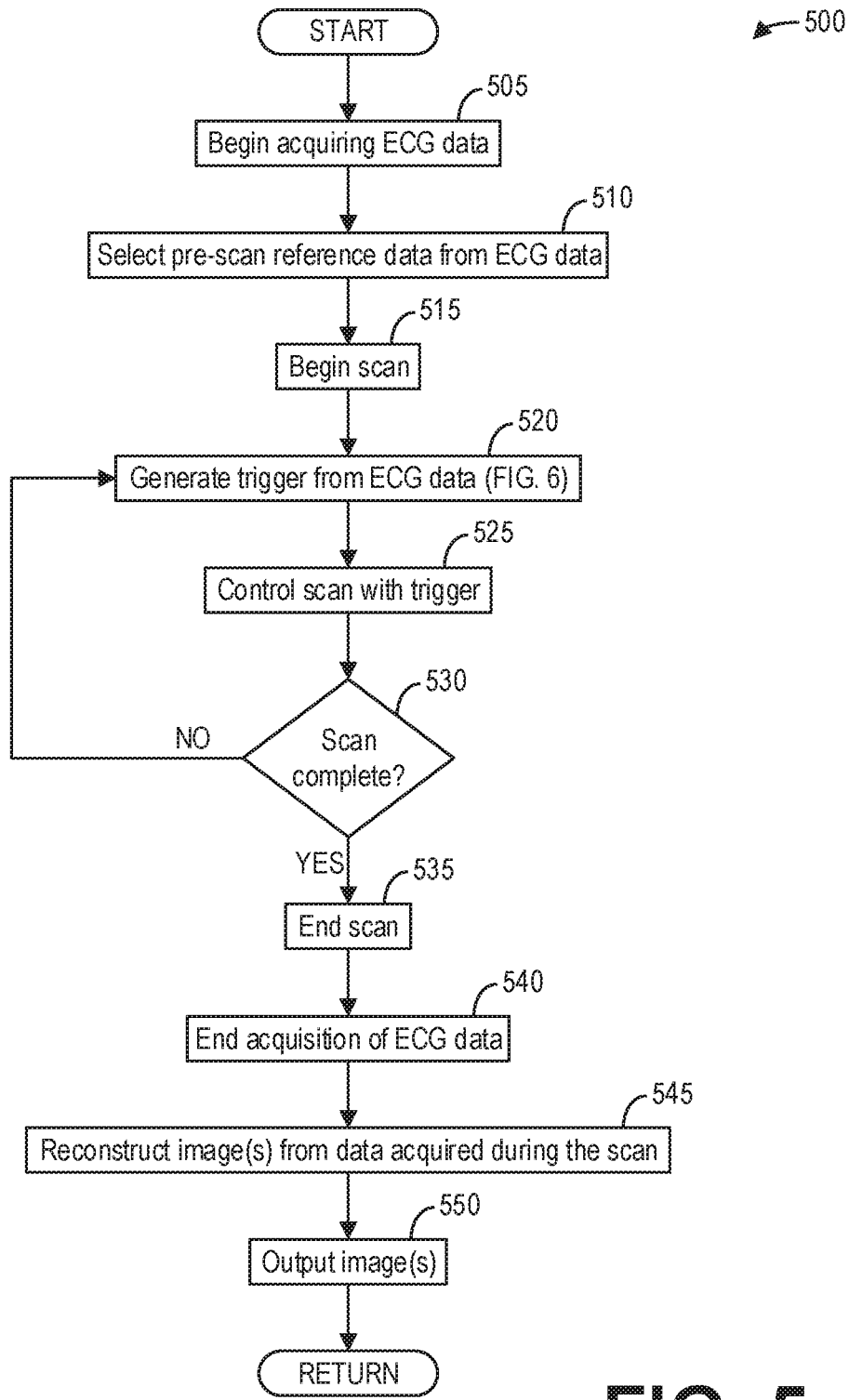
FIG. 5 shows a high-level flow chart illustrating an example method for triggering MR data acquisition according to an embodiment.

FIG. 5 shows a high-level flow chart illustrating an example method 500 for triggering MR data acquisition according to an embodiment. In particular, method 500 relates to controlling an MRI scan of a subject with a trigger determined from ECG data of the subject. Method 500 is described with reference to the systems and components of FIGS. 1-4, though it should be appreciated that the method 500 may be implemented with other systems and components without departing from the scope of the present disclosure. Method 500 may be stored as executable instructions distributed across one or more non-transitory memories of the MRI apparatus 10, such as the non-transitory memory 91 of the ECG signal analyzer 88, and may be executable by one or more processors of the MRI apparatus 10, such as the controller unit 25 and the processor 90 of the ECG signal analyzer 88.

Method 500 begins at 505. At 505, method 500 begins acquiring ECG data of the subject or patient. For example, method 500 may begin receiving ECG data of the subject 16 via the ECG sensors 85*a* and 85*b*. At 510, method 500 selects pre-scan reference data from the ECG data. For example, method 500 may select, via the ECG signal analyzer 88, pre-scan reference data acquired by the ECG sensors 85*a* and 85*b*. The pre-scan reference data comprises ECG data of the subject 16 when the ECG sensors 85*a* and 85*b* are not subjected to various magnetic fields and RF signals that may be generated by the MRI apparatus 10 during a scan of the subject 16, which may consequently introduce noise into the ECG signal during the scan. As discussed herein, the pre-scan reference data is utilized for assisting in the detection of R-peaks in the ECG data acquired during the scan.

After acquiring the reference data, method 500 continues to 515. At 515, method 500 begins the scan. To that end, method 500 may control the controller unit 25 to issue various control signals to the RF driver unit 22, the gradient coil driver unit 23, and the data acquisition unit 24 to begin scanning the subject 16 as described hereinabove with regard to FIG. 1.

After beginning the scan, method 500 proceeds to 520. At 520, method 500 generates a trigger from the ECG data acquired via the ECG sensors 85*a* and 85*b*. For example, if R-peaks in the ECG data are to be used for triggering data acquisition, method 500 may provide the ECG data or ECG signal to one or more R-peak detection classifiers for detecting an R-peak in the ECG data. An example method for generating a trigger from ECG data is described further herein with regard to FIG. 6.

At 525, method 500 controls the scan with the trigger. For example, method 500 may control the data acquisition unit 24 to acquire image data responsive to the trigger. As mentioned above and described further herein, the trigger comprises the robust detection of an R-peak in the ECG data. Thus, once the R-peak is detected, method 500 is triggered to perform data acquisition via the data acquisition unit 24.

Continuing at 530, method 500 determines if the scan is complete. If the scan is not complete ("NO"), method 500 returns to 520, wherein method 500 continues the scan and determines another trigger from ECG data. However, if the scan is complete ("YES"), method 500 continues to 535, wherein method 500 ends the scan. Further, at 540, method 500 ends the acquisition of the ECG data.

Continuing at 545, method 500 reconstructs one or more images from data acquired during the scan. The one or more images may be reconstructed, for example by the data processing unit 31, by applying any suitable image reconstruction algorithm to the image data acquired during the scan. At 550, method 500 outputs the one or more images. The one or more images may be output, for example, to a display such as display unit 33. Additionally or alternatively, the one or more images may be output to memory for subsequent retrieval and review. Method 500 then ends.

As the one or more images are reconstructed from image data acquired responsive to the trigger, the one or more images may include a reduced number of motion artifacts that would otherwise be present. In order to ensure that the MR data acquisition optimally occurs during the period of least heart motion, the trigger should correspond to a robust detection of an R-peak in the ECG data. As an illustrative example, FIG. 6 shows a high-level flow chart illustrating an example method 600 for generating a trigger from ECG data according to an embodiment. In particular, method 600 relates to detecting an R-peak in a sample of ECG data to determine a trigger. Method 600 is described with reference to the systems and components of FIGS. 1-4, as well as the method of FIG. 5, though it should be appreciated that the method 600 may be implemented with other systems, components, and methods without departing from the scope of the present disclosure. Method 600 may be stored as executable instructions in non-transitory memory, such as non-transitory memory 91, of the ECG signal analyzer 88, and executed by the processor 90 of the ECG signal analyzer 88.

Method 600 begins at 605. At 605, method 600 pre-processes ECG data into a sample. The sample of ECG data may comprise a plurality of discrete measurements of the ECG signal or ECG data over time during a given duration or temporal length. For example, as discussed hereinabove, the sample may comprise one or two thousand discrete measurements of the ECG signal over a two-second duration. Further, method 600 may pre-process a first channel of ECG data into a first sample and a second channel of ECG data into a second sample, as discussed hereinabove with regard to FIG. 2. An example method for pre-processing ECG data into a sample is described further herein with regard to FIG. 7.

In addition to pre-processing real-time ECG data acquired during the scan into a sample, method 600 also pre-processes the pre-scan reference data acquired at 510 into a reference sample. Method 600 pre-processes the pre-scan reference data into the reference sample with the same pre-processing steps applied to the real-time ECG data.

Continuing at 610, method 600 determines a signal quality of the sample. Method 600 may, for example, input the sample into a signal quality classifier such as the first signal quality classifier 222 or the second signal quality classifier 224. More specifically, method 600 inputs the first sample pre-processed at 605 into the first signal quality classifier 222, and inputs the second sample pre-processed at 605 into the second signal quality classifier 224. The first and second signal quality classifiers 222 and 224 output an indication of whether the signal quality of the respective samples is good or bad.

At 615, method 600 detects an R-peak in the sample. To that end, method 600 inputs the sample into an R-peak detection classifier such as the first R-peak detection classifier 223 or the second R-peak detection classifier 225. More specifically, method 600 inputs the first sample pre-processed at 605 into the first R-peak detection classifier 223 and the second sample pre-processed at 605 into the second R-peak detection classifier 225. Furthermore, method 600 may also input the reference sample pre-processed at 605 into the R-peak detection classifiers 223 and 225 to improve the robustness of detecting the R-peaks in the samples. The first R-peak detection classifier 223 and the second R-peak detection classifier 225 output an indication of whether the respective samples include an R-peak.

At 620, method 600 determines if an R-peak is detected in the sample(s). If an R-peak is not detected in the sample(s) ("NO"), method 600 continues to 625. At 625, method 600 discards the sample(s). Method 600 then continues to 630, wherein method 600 steps forward temporally in the ECG data. Method 600 then returns to 605 to pre-process the ECG data into a sample. The time step may be set relatively small relative to the temporal length of the samples, such that the subsequent sample pre-processed at the second iteration of 605 overlaps temporally with the first sample. In this way, if the R-peak occurs right after the end of the first iteration, the R-peak will be observable near the end of the samples in the second iteration and so the R-peak will be detected in the second iteration. To that end, method 600 may step forward by five to ten milliseconds, for example, such that the difference between the beginning of the sample in the first iteration and the beginning of the sample in the second iteration is five to ten milliseconds. It should be appreciated that in some examples, method 600 may take longer time steps than five to ten milliseconds between iterations, or may even take shorter time steps than five to ten milliseconds.

Referring again to 620, if an R-peak is detected in the sample ("YES"), method 600 continues to 635. At 635, method 600 generates a trigger according to the signal quality and the detected R-peak. An example method for generating a trigger according to the signal quality and the detected R-peak is described further herein with regard to FIG. 9. Briefly, the trigger may only be generated if the signal quality of the sample is good. In this way, the method may be avoid triggering data acquisition according to false positives or noise peaks in the ECG data that only resemble R-peaks.

At 640, method 600 outputs the trigger generated at 635. As discussed hereinabove, method 500 may control the scan with the trigger output at 640. Method 600 then returns.

FIG. 7 shows a high-level flow chart illustrating an example method 700 for pre-processing ECG data for triggering MR data acquisition according to an embodiment. Method 700 is described with reference to the systems and components of FIGS. 1-4, as well as the methods of FIGS. 5 and 6, though it should be appreciated that the method 700 may be implemented with other systems, components, and methods without departing from the scope of the present disclosure. As an example, method 700 may be stored as executable instructions in non-transitory memory 91 of the ECG signal analyzer 88, and may be executed by the processor 90 of the ECG signal analyzer 88.

Method 700 begins at 705. At 705, method 700 converts the ECG data into millivolts. For example, method 700 may convert the ECG data from digit values to millivolts using known PAC gain factors. At 710, method 700 processes the ECG data into a sample with a given temporal length. For example, method 700 may discretely sample the ECG data over time for the given temporal length or duration. As mentioned above, method 700 may discretely sample the ECG data thousands of times, such as two thousand times, over a duration of two seconds, such that the sample includes two thousand measurements. Continuing at 715, method 700 applies one or more filters to the sample. For example, method 700 may apply three passband filters to the sample. The first passband filter may comprise a 1-35 Hz filter, the second passband filter may comprise a 5-15 Hz filter, and the third passband filter may comprise a 15-30 Hz filter.

As an illustrative example, FIG. 8 shows a set of graphs 800 illustrating pre-processed ECG data for triggering MR data acquisition according to an embodiment. In particular, the first graph 805 depicts a raw or unfiltered sample of the ECG data wherein no passband filter is applied; the second graph 810 depicts a first filtered sample of the ECG data wherein the first 1-35 Hz passband filter is applied to the raw sample depicted by the first graph 805; the third graph 815 depicts a second filtered sample of the ECG data wherein the second 5-15 Hz passband filter is applied to the raw sample depicted by the first graph 805; and the fourth graph 820 depicts a third filtered sample of the ECG data wherein the third 15-30 Hz passband filter is applied to the raw sample depicted by the first graph 805. A sample as discussed hereinabove with regard to FIG. 8 may comprise the raw sample depicted by the first graph 805 as well as the filtered samples depicted by the graphs 810, 815, and 820.

The set of graphs 800 further includes a plurality of graphs depicting a reference sample. In particular, the fifth graph 807 depicts a raw or unfiltered reference sample of the pre-scan ECG data wherein no passband filter is applied, the sixth graph 812 depicts a first filtered reference sample of the pre-scan ECG data wherein the first passband filter is applied, the seventh graph 817 depicts a second filtered reference sample of the pre-scan ECG data wherein the second passband filter is applied, and the eighth graph 822 depicts a third filtered reference sample of the pre-scan ECG data wherein the third passband filter is applied. An R-peak is distinctly visible near the two second mark in the reference sample as depicted by the graphs 807, 812, 817, and 822. By providing the reference sample illustrated by the graphs 807, 812, 817, and 822 along with the real-time sample illustrated by the graphs 805, 810, 815, and 820, the R-peak detection classifiers described hereinabove may reliably detect an R-peak in the real-time sample.

Referring again to FIG. 7, after applying the one or more filters to the sample to create the pre-processed samples which may be used as described hereinabove to detect an R-peak, method 700 then returns.

FIG. 9 shows a high-level flowchart illustrating an example method 900 for determining a trigger according to an embodiment. Method 900 is described with reference to the systems and components of FIGS. 1-4, as well as the methods of the convolutional network, though it should be understood that the method 900 may be implemented with other systems and components without departing from the scope of the present disclosure. Method 900 may be implemented as executable instructions in the non-transitory memory 91 of the ECG signal analyzer 88 and may be executed by the processor 90 of the ECG signal analyzer 88.

Method 900 begins at 905. At 905, method 900 receives the signal quality and R-peak classifier output for the first ECG signal and the second ECG signal. As discussed hereinabove, the signal quality output for the first and second ECG signals comprises an indication that the signal is good or bad, while the R-peak classifier output comprises an indication of whether an R-peak is detected in the sample.

At 910, method 900 determines if the signal quality of the first ECG signal and the second ECG signal are good. If the signal quality of both signals is good ("YES"), method 900 continues to 915. At 915, method 900 outputs an average of the R-peak classifier output for the first ECG signal and the second ECG signal. The average of the R-peak classifier output may account for phase differences between the different ECG channels, such that the trigger incorporates information from both channels. Method 900 then returns.

However, if the signal quality of both signals is not good ("NO"), method 900 continues to 920. At 920, method 900 determines if the signal quality of both signals is bad. If the signal quality of both signals is bad ("YES"), method 900 continues to 925. At 925, method 900 outputs no trigger and further outputs an indication of bad signal quality. The indication of bad signal quality may be displayed to an operator of the MRI apparatus 10 via the display unit 33, for example, if an indication of bad signal quality is output for a threshold number of iterations during a scan. For example, if three or more iterations result in an output of bad signal quality, the indication may be displayed to the operator such that the operator may be prompted to adjust or replace the ECG sensors 85*a* and 85*b* on the subject 16. The indication may further specify which of the ECG sensors 85*a* and 85*b* to adjust or replace. Method 900 then ends.

However, if the signal quality of both signals is not bad ("NO"), method 900 continues to 930. At 930, method 900 determines if the signal quality of the first ECG signal is good. If the signal quality of the first ECG signal ECG1 is good ("YES"), method 900 continues to 935. At 935, method 900 outputs the R-peak classifier output for the first ECG signal as the trigger. Method 900 then returns.

However, if the signal quality of the first ECG signal is not good ("NO"), method 900 continues to 940. Since the quality of both signals is neither good nor bad, and the signal quality of the first ECG signal is not good, then the signal quality of the second ECG signal must be good. Thus, at 940, method 900 outputs the R-peak classifier output of the second ECG signal as the trigger. Method 900 then ends.

A technical effect of the disclosure includes triggering image data acquisition responsive to detecting an R-peak in an ECG signal. Another technical effect of the disclosure includes controlling one or more components of an imaging system according to output of one or more convolutional neural networks.

Furthermore, while the methods described herein are described with regard to an MM apparatus or system, one of ordinary skill in the art will appreciate that the methods may be implemented with any imaging modality suitable for triggering responsive to periodic physiological motion.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
   acquiring, during a scan of a subject, an electrical signal indicating a periodic physiological motion of an organ of the subject;
   pre-processing the electrical signal to generate a plurality of samples,
   wherein the plurality of samples comprise a first sample and a second sample, and
   wherein the first sample and the second sample comprises a plurality of discrete measurements of the electrical signal over time during the scan;
   inputting the first sample of the electrical signal into a trained neural network to detect whether a peak is present in the first sample;
   triggering acquisition of image data responsive to detecting the peak in the first sample;
   not triggering the acquisition of image data responsive to not detecting the peak in the first sample; and
   responsive to not detecting the peak in the first sample, discarding the first sample, inputting the second sample of the electrical signal into the trained neural network, and triggering the acquisition of image data responsive to detecting the peak in the second sample,
   wherein the second sample at least partially temporally overlaps the first sample in the electrical signal.

2. The method of claim 1, wherein pre-processing the electrical signal further comprises converting the electrical signal from digital values to millivolts.

3. The method of claim 1, wherein the plurality of discrete measurements of the electrical signal over time during the scan comprises a raw sample, and wherein pre-processing the electrical signal further comprises applying one or more bandpass filters to the raw sample to generate one or more filtered samples, wherein the first sample comprises the raw sample and the one or more filtered samples.

4. The method of claim 1, further comprising acquiring a reference signal indicating the periodic physiological motion of the organ of the subject prior to the scan of the subject to generate a reference sample, and inputting the reference sample with the first sample to the trained neural network.

5. The method of claim 4, wherein the reference signal comprises electrocardiograph (ECG) data of the subject when ECG sensors were not subjected to magnetic fields and radio frequency (RF) signals.

6. The method of claim 1, further comprising inputting the first sample into a signal quality classifier to determine whether a signal quality of the first sample is degraded, and rejecting output of the trained neural network responsive to the signal quality of the first sample being degraded.

7. The method of claim 1, wherein the organ comprises a heart, and wherein the electrical signal comprises an electrocardiogram.

8. The method of claim 7, wherein the trained neural network comprises a convolutional neural network, and wherein the peak comprises an R-peak of the electrocardiogram.

9. The method of claim 1, wherein the trained neural network includes three output nodes: peak presence, no peak presence, and non-peak spike noise.

10. A method, comprising:
    acquiring, during a diagnostic scan of a subject, a first channel and a second channel of an electrical signal indicating periodic physiological motion of an organ of the subject;

pre-processing the first channel and the second channel of the electrical signal into a first sample and a second sample, respectively, wherein the first sample and the second sample comprises a plurality of discrete measurements of the electrical signal over time during the diagnostic scan;

inputting the first sample into a first trained neural network to detect whether a peak in the periodic physiological motion is present in the first sample;

inputting the second sample into a second trained neural network to detect whether the peak is present in the second sample, wherein the first channel is different from the second channel, and wherein the second sample at least partially temporally overlaps the first sample in the electrical signal;

determining presence of the peak by combining detections of the first trained neural network and the second trained neural network; and triggering acquisition of image data responsive to determining that the peak is present.

11. The method of claim 10, further comprising: inputting the first sample into a first signal quality classifier to determine the signal quality of the first sample; inputting the second sample into a second signal quality classifier to determine the signal quality of the second sample; and determining presence of the peak by combining detections of the first trained neural network and the second trained neural network, and the signal quality of the first sample and the second sample.

12. The method of claim 11, further comprising:

responsive to the signal quality of the first sample and the signal quality of the second sample both being not degraded, determining a timing of triggering according to a phase-corrected average of output from a first peak detection classifier and output from a second peak detection classifier;

responsive to the signal quality of the first sample being not degraded and the signal quality of the second sample being degraded, determining the timing according to the output of the first peak detection classifier; and responsive to the signal quality of the first sample being degraded and the signal quality of the second sample being not degraded, determining the timing according to the output of the second peak detection classifier.

13. The method of claim 12, further comprising, responsive to the signal quality of the first sample being degraded and the signal quality of the second sample being degraded, not triggering the acquisition of image data, and outputting an indication that the acquisition of the electrical signal is degraded.

14. A system, comprising:

a medical scanning system for scanning a subject;

an electrocardiograph (ECG) sensor positioned on the subject for generating an ECG signal; and a processor communicatively coupled to the medical scanning system and the ECG sensor and configured to:

acquire a reference ECG signal from the subject via the ECG sensor prior to a scan of the subject to generate a reference sample;

acquire, during the scan, the ECG signal via the ECG sensor;

pre-processing the ECG signal into a sample that comprises a plurality of discrete measurements of the ECG signal over time during the scan;

input both the sample of the ECG signal and the reference sample into a trained neural network to detect whether a peak is present in the sample;

trigger acquisition of image data by the medical scanning system responsive to detecting the peak in the sample; and not trigger the acquisition of image data by the medical scanning system responsive to not detecting the peak in the sample.

15. The system of claim 14, wherein the plurality of discrete measurements of the ECG signal over time during the scan comprises a raw sample, and wherein pre-processing the ECG signal further comprises applying one or more passband filters to the raw sample to generate one or more filtered samples, wherein the sample comprises the raw sample and the one or more filtered samples.

* * * * *